US00PP30749P3

(12) United States Plant Patent
van Langen

(10) Patent No.: US PP30,749 P3
(45) Date of Patent: Jul. 23, 2019

(54) ***CRASSULA* PLANT NAMED 'AMICRA1701'**

(50) Latin Name: *Crassula arborescens*
Varietal Denomination: AMICRA1701

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/998,368

(22) Filed: Aug. 9, 2018

(65) Prior Publication Data

US 2019/0053415 P1 Feb. 14, 2019

(30) Foreign Application Priority Data

Aug. 9, 2017 (QZ) ..... PBR 2017/1946

(51) Int. Cl.
*A01H 5/12* (2018.01)
*A01H 6/32* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct variety of *Crassula* plant named 'AMICRA1701' which is characterized by the combination of a broad spreading to upright and freely-branching growth habit, an abundance of strong and thick foliage, glaucous greyed-green foliage which is margined and sparsely dotted red, and the stability of all characteristics from generation to generation.

2 Drawing Sheets

Latin name of the genus and species: The Latin name of the genus and species of the novel variety disclosed herein is *Crassula arborescens*.

Variety denomination: The inventive variety of *Crassula* disclosed herein has been given the variety denomination 'AMICRA1701'.

CROSS REFERENCE TO RELATED APPLICATIONS

This application claims priority to the Community Plant Variety Rights application number 2017/1946, filed Aug. 9, 2017, which is herein incorporated by reference.

BACKGROUND OF THE INVENTION

Parentage: 'AMICRA1701' originated as a naturally occurring, branch mutation of an unnamed *Crassula arborescens* plant (not patented). In November 2016, the inventor discovered the mutation at his commercial greenhouse in Heerhugowaard, The Netherlands, growing amongst a cultivated population of *Crassula arborescens* plants. The mutated branch was noted for its greyed-green foliage with red margins. Cuttings were taken from the mutated branch, rooted, and then grown out for further evaluation in order to confirm the distinctness and stability of the characteristics first observed. Upon confirmation of distinctness and stability, 'AMICRA1701' was selected for commercialization in January of 2017.

Asexual Reproduction: Asexual reproduction of 'AMICRA1701', by way of stem cuttings, was first initiated in January of 2017 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMICRA1701' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'AMICRA1701'. These characteristics in combination distinguish 'AMICRA1701' as a new and distinct *Crassula* cultivar:

1. *Crassula* 'AMICRA1701' exhibits a freely branching, broad to upright growth habit; and
2. *Crassula* 'AMICRA1701' exhibits an abundance of strong, thick foliage; and
3. *Crassula* 'AMICRA1701' exhibits glaucous greyed-green foliage which is margined and sparsely dotted red.

BOTANICAL DESCRIPTION OF THE PLANT

Figure 1:
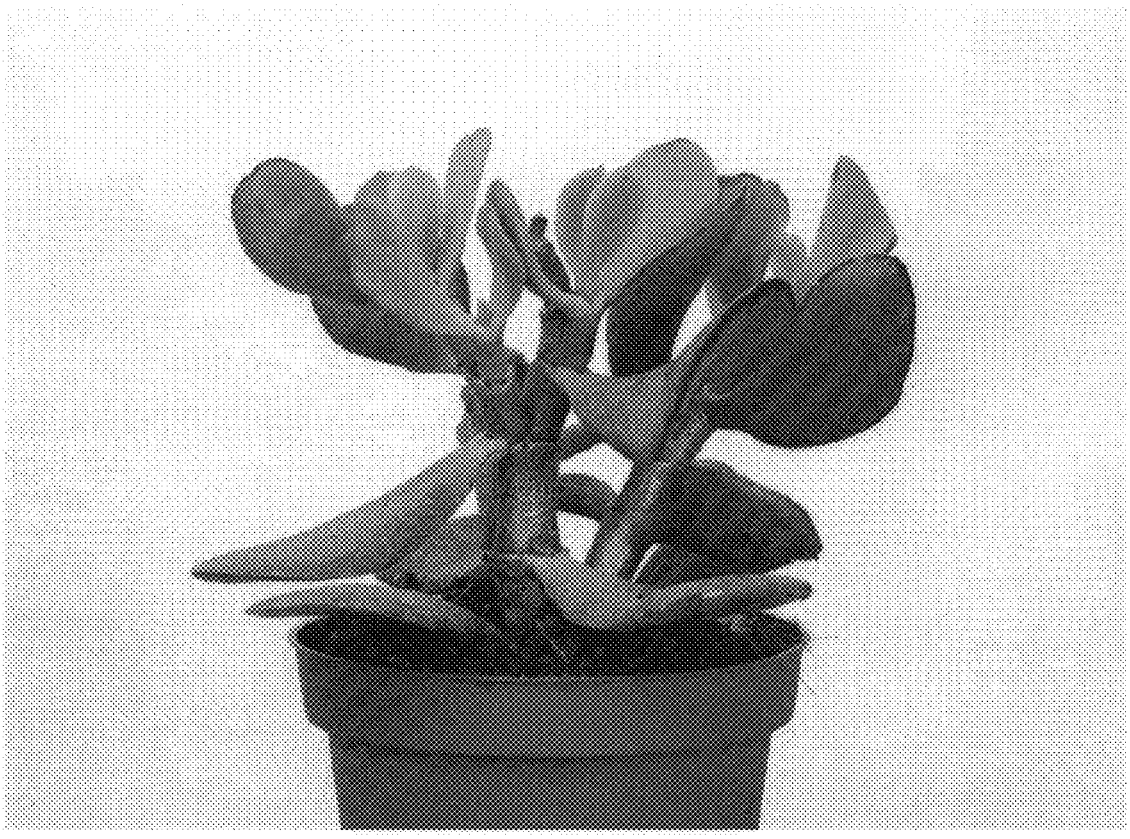
FIG. 1 illustrates, as nearly true as it is reasonably possible to make the same in color photographs of this type, an exemplary plant of 'AMICRA1701' grown in a grown in a commercial greenhouse in Heerhugowaard, The Netherlands. This plant is approximately 6 months old, shown planted in an 11 cm container.
Figure 2:
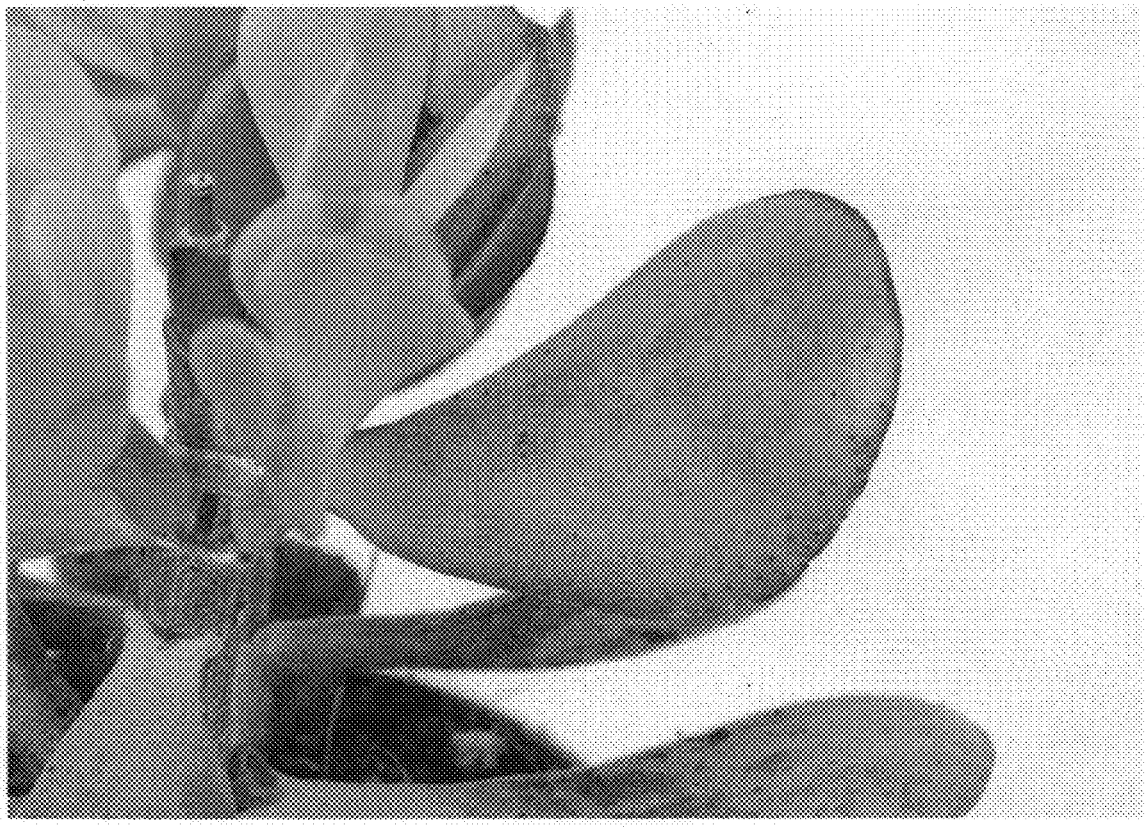
FIG. 2 illustrates, as nearly true as it is reasonably possible to make the same in color photographs of this type, the typical foliage of 'AMICRA1701'.

The following observations and measurements made in October of 2017 describe averages from a sample set of six specimens of 6 month-old 'AMICRA1701' plants grown in 17 cm nursery containers at commercial greenhouse in Heerhugowaard, the Netherlands. Plants were produced using conventional greenhouse production protocols for *Crassula* plants which consisted of minimal irrigation and fertilizer applications, as well as chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMICRA1701' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'AMICRA1701' and comparisons with the parent and closest known commercial comparator are provided below.

Plant description:

*Growth habit.*—Broad spreading to upright perennial.

*Plant form.*—Irregular broad obovate to flattened globular.

*Average height.*—10.0 cm from the soil level to the top of the foliar plane.

*Plant spread.*—Average of 15.7 cm.

*Growth rate.*—Low to moderate.

*Plant vigor.*—Moderate.

*Propagation type.*—Stem cuttings.

*Time to initiate rooting.*—Approximately 21 days at 18 degrees Celsius.

*Time to produce a finished plant.*—Approximately 6 months.

*Disease resistance.*—Neither resistance nor susceptibility to typical *Crassula* pests and diseases has been observed.

*Environmental tolerances.*—Adapt to, at least, USDA Zones 10 and 12 and temperatures as high as 40 degrees Celsius; low tolerance to rain; moderate to high tolerance to wind.

Root system:

*General.*—Dense and freely branched rooting; roots are moderately fibrous.

*Distribution in the soil profile.*—Shallow to moderately deep.

*Diameter of roots.*—0.1 cm on average.

*Texture.*—Smooth and glabrous.

*Color.*—Greyed-orange, nearest to RHS 165B.

Stem:

*General branching habit.*—Basally branching main stems; freely branching with lateral branches. Pinching isn't required but will improve branching.

*Quantity of main stems per plant.*—2.

*Quantity of lateral branches.*—8.

*Length of lateral branches.*—Approximately 2.5 cm.

*Diameter of lateral branches.*—Approximately 0.6 cm.

*Internode length.*—Approximately 1.6 cm.

*Attitude.*—At an average angle of 40 degrees to vertical, varying between 30 and 50 degrees.

*Cross-section.*—Rounded.

*Texture.*—Glabrous; succulent.

*Luster.*—Matte.

*Strength.*—Strong.

*Color, juvenile.*—Yellow-green, nearest to RHS 144A.

*Color, mature.*—Green, nearest to RHS 143C.

*Color at internodes.*—Green, nearest to RHS 143C.

*Color of the oldest wood.*—Greyed-brown, nearest to a combination of RHS 199A, 199B and 199C.

Foliage:

*Arrangement.*—Opposite.

*Division.*—Simple.

*Quantity.*—6 paired leaves per lateral branch.

*Attitude.*—Upward.

*Lamina.*—Shape — Obovate to broad spatulate. Aspect — Slightly concave. Dimensions — 6.8 cm long and 3.8 cm wide. Thickness — Approximately 0.5 cm. Apex — Rounded. Base — Cuneate. Margin — Entire. Texture of top surface — Glabrous, succulent, and glaucous. Texture of bottom surface — Glabrous, succulent, and glaucous. Color — Juvenile foliage, adaxial surface — Yellow-green, nearest to in between RHS 144A and 146D. Juvenile foliage, abaxial surface — Yellow-green, nearest to in between RHS 144A and 146D. Mature foliage, adaxial surface — Nearest to in between green, RHS 137B, and yellow-green, RHS 147B; margined and sparsely dotted greyed-purple, nearest to a combination of RHS 187B and 187C; the epicuticular glaucous wax covering the leaf surface is greyed-green, nearest to RHS 194B. Mature foliage, abaxial surface — Yellow-green, nearest to RHS 147B; margined and sparsely dotted greyed-purple, nearest to in between RHS N186C and 187A; the epicuticular glaucous wax covering the leaf surface is greyed-green, nearest to RHS 194B. Venation — No veins are visible.

*Petiole.*—No petioles present, leaves sessile.

Inflorescence: No flowering has been observed to date.

COMPARISON WITH THE PARENT PLANT

Plants of the new cultivar 'AMICRA1701' differs from the parent, an unnamed *Crassula arborescens* plant (not patented), in the following characteristics described in Table 1 below.

TABLE 1

| Characteristic | 'AMICRA1701' | The parent. |
|---|---|---|
| Plant vigor. | More vigorous than the parent; lower mortality rate in propagation. | Less vigorous; higher mortality rate in propagation. |
| Branching habit. | More freely branching. | Less branched. |
| Stem strength. | Stronger than the parent. | Weaker than 'AMICRA1701'. |
| General coloration of the foliage. | Greyed green and more narrowly margined red. | Green and more broadly margined red. |

COMPARISON WITH THE CLOSEST KNOWN COMPARATOR

Plants of the new cultivar 'AMICRA1701' differs from the species, *Crassula ovata* (not patented), in the following characteristics described in Table 2 below.

TABLE 2

| Characteristic | 'AMICRA1701' | *Crassula ovata* |
|---|---|---|
| Branching habit. | More freely branching. | Less branched. |
| Stem strength. | Stronger than *Crassula ovata*. | Weaker than 'AMICRA1701'. |
| General coloration of the foliage. | Greyed green and margined red. | Green and margined red. |

That which is claimed is:

1. A new and distinct variety of *Crassula* plant named 'AMICRA1701', substantially as described and illustrated herein.

* * * * *